(12) United States Patent
Wei et al.

(10) Patent No.: US 11,591,330 B2
(45) Date of Patent: Feb. 28, 2023

(54) HIF-2A SMALL-MOLECULE INHIBITOR AND USE THEREOF

(71) Applicant: China Medical University, Liaoning (CN)

(72) Inventors: Minjie Wei, Liaoning (CN); Yuanyuan Yan, Liaoning (CN); Miao He, Liaoning (CN); Yinuo Liu, Liaoning (CN); Liwen Zhang, Liaoning (CN)

(73) Assignee: China Medical University, Liaoning (CN)

( * ) Notice: Subject to any disclaimer, the term of this patent is extended or adjusted under 35 U.S.C. 154(b) by 168 days.

(21) Appl. No.: 16/969,396

(22) PCT Filed: Jan. 25, 2019

(86) PCT No.: PCT/CN2019/073097
§ 371 (c)(1),
(2) Date: Aug. 12, 2020

(87) PCT Pub. No.: WO2019/154104
PCT Pub. Date: Aug. 15, 2019

(65) Prior Publication Data
US 2021/0053966 A1    Feb. 25, 2021

(30) Foreign Application Priority Data
Feb. 12, 2018    (CN) .......................... 201810146778.1

(51) Int. Cl.
*C07D 471/04*    (2006.01)

(52) U.S. Cl.
CPC ................. *C07D 471/04* (2013.01)

(58) Field of Classification Search
CPC ................................................... C07D 471/04
See application file for complete search history.

(56) References Cited

FOREIGN PATENT DOCUMENTS

| CN | 1809563 | * | 7/2006 | ........... C07D 471/04 |
| WO | WO2016/144826 | * | 9/2016 | ........... C07D 417/04 |

OTHER PUBLICATIONS

STN Registry No. 1223759-43-0 (2010).*
Vippagunta et al. (2001).*
Banker et al. (1997).*
Wolff et al. (1995).*

* cited by examiner

*Primary Examiner* — Paul V Ward
(74) *Attorney, Agent, or Firm* — Houtteman Law LLC

(57) ABSTRACT

The present invention belongs to the field of diagnosis and treatment of tumors, and relates to a HIF-2α small-molecule inhibitor and use thereof in treatment of tumors such as breast cancer and ovarian cancer. The small-molecule inhibitor is a compound represented by formula (I) or a stereoisomer, pharmaceutically acceptable salt, solvate or prodrug of the compound represented by formula (I). The small-molecule inhibitor mainly inhibits the proliferation of tumor cells by inhibiting HIF-2α protein, and can also inhibit the growth of CSCs with high expression of HIF-2α. The small-molecule inhibitor can be used as a novel anti-tumor drug to completely eliminate tumors and stem cells, and has broad application prospects.

4 Claims, 4 Drawing Sheets

HIF-2A SMALL-MOLECULE INHIBITOR AND USE THEREOF

TECHNICAL FIELD

The present invention belongs to the field of diagnosis and treatment of tumors, and relates to a HIF-2α small-molecule inhibitor and use thereof in treatment of tumors such as breast cancer and ovarian cancer.

BACKGROUND

Cancer is a malignant tumor, which generally refers to abnormal cell differentiation and proliferation, and out-of-control growth of normal cells in a body due to external stimuli and has invasion and metastasis. Cancer stem cells (CSCs) are also known as "tumor initiating cells". CSCs have been found in a wide variety of tumors such as breast cancer and ovarian cancer. CSCs are the seeds of tumor occurrence and recurrence, have strong self-renewal ability and multidirectional differentiation potential, and are the root cause of tumor drug resistance. Because CSCs are in a dormant state, their ability to both divide and proliferate is weak. However, current radiotherapy and chemotherapy are mainly aimed at cells at a high proliferation and division stage, so CSCs cannot be effectively targeted and killed, thus resulting in tumor cell metastasis and recurrence.

Paclitaxel is a common chemotherapeutic drug for the treatment of breast cancer, and cisplatin is a common chemotherapeutic drug for the treatment of ovarian cancer. However, long-term treatment with chemotherapeutic drugs such as paclitaxel and cisplatin may induce the production of CSCs and mediate drug resistance. Therefore, targeting CSCs to develop novel drugs against tumors such as breast cancer and ovarian cancer is of great significance for improving the clinical treatment of tumors.

Solid tumors such as breast cancer and ovarian cancer exist in a hypoxic microenvironment. The hypoxic microenvironment can mediate tumor cell resistance to radiotherapy and chemotherapy by promoting tumor angiogenesis and inducing CSCs-like phenotypic transformation. Hypoxia inducible factor (HIFs) oxygen content-sensitive a subunit isomer HIF-1/2α is degraded by means of ubiquitination in normoxia. Moreover, under hypoxic conditions, HIF-1/2α is stably incorporated into the nucleus to initiate transcriptional expression of downstream target genes, thereby enabling tumor cells to tolerate the hypoxic environment. Recent studies have shown that HIF-2α plays an important role in maintaining the sternness and undifferentiated state of tumor cells. The development of targeted inhibitory drugs for HIF-2α is of great significance.

At present, there are few reports on HIF-2α inhibitors. Only Cho et al. found small-molecule PT2399 that can have targeted inhibition of pVHL-deficient renal carcinoma cells HIF-2α, but there are no reports of HIF2-α inhibitors for other tumors such as breast cancer and ovarian cancer. Therefore, developing a novel inhibitor that can target specifically and highly expressed HIF-2α in tumor stem cells has very important clinical significance for inhibiting tumor occurrence, metastasis and recurrence.

SUMMARY

The present invention aims to solve one of the problems in the existing anti-tumor drug research and development technology, such as the targeted inhibitory effect on CSCs. Therefore, one object of the present invention is to propose a superior structural compound having high anti-tumor and anti-CSCs activity and a HIF-2α inhibiting effect.

In order to achieve the above-mentioned object, the present invention adopts the following technical solutions:

A first aspect of the present invention relates to a compound of general formula (I), or a stereoisomer, pharmaceutically acceptable salt or solvate thereof.

A second aspect of the present invention relates to a pharmaceutical composition containing the compound of general formula (I), or the stereoisomer, pharmaceutically acceptable salt or solvate thereof.

A third aspect of the present invention relates to an application of the compound of general formula (I), or the stereoisomer, pharmaceutically acceptable salt or solvate thereof in preparation of drugs for preventing or treating cell proliferative and cell regenerative diseases, especially cancers such as breast cancer and ovarian cancer.

A HIF-2α small-molecule inhibitor, which is a compound represented by formula (I) or a stereoisomer, pharmaceutically acceptable salt, solvate or prodrug of the compound represented by formula (I),

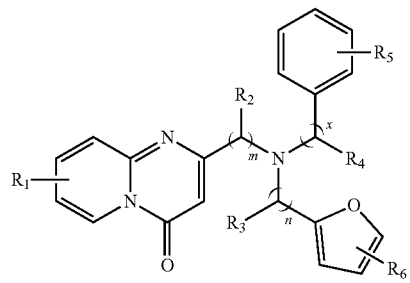

where:

m represents 0, 1, 2 or 3; n represents 0, 1, 2 or 3; and x represents 0, 1, 2 or 3;

R1 is an optionally mono- or poly-substituted substituent at any position on a parent nucleus based on pyrimido[1,2-a]pyridine; R2, R3 and R4 are substituents on any carbon atoms on a 2-position branch of a pyrimido[1,2-a]pyridine-based parent nucleus ring; R5 is an optionally mono- or poly-substituted substituent at any position on a benzene ring; R6 is an optionally mono- or poly-substituted substituent at any position on a furan ring; the substituted substituent is one or more selected from C1-6 alkyl, halogen-, hydroxyl-, carboxyl- or cyano-substituted C1-6 alkyl, halogen-, hydroxyl-, carboxyl- or cyano-substituted C3-6 cycloalkyl, C1-6 alkoxyl, halogen-, hydroxyl-, carboxyl- or cyano-substituted C1-6 alkoxyl, C2-6 alkenyl, halogen-, hydroxyl-, carboxyl- or cyano-substituted C2-6 alkenyl, nitro, amino, C1-6 alkyl-substituted amino, halogen, cyano, sulfo, hydroxyl, carboxyl, phenyl, and heterocyclyl; and two adjacent substituent groups and linking atoms form a three-membered, four-membered, five-membered or multi-membered ring structure.

The "halogen" or "halo" in the present invention refers to fluorine, chlorine, bromine or iodine serving as a substituent. When a halogen atom serves as a substituent, the number of substitutions thereof is more than one, including one, two or three, etc.

The "$C_{1-6}$ alkyl" in the present invention refers to linear or branched alkyl derived from removing one hydrogen atom on alkane containing 1-6 carbon atoms.

The "C$_{2-6}$ alkenyl" in the present invention refers to linear or branched or cyclic alkenyl having 2-6 carbon atoms containing a carbon-carbon double bond. The "C$_{2-6}$ alkynyl" in the present invention refers to linear or branched alkynyl having 2-6 carbon atoms containing a carbon-carbon triple bond, and the "C$_{2-7}$ alkynyl" refers to linear or branched alkynyl having 2-7 carbon atoms containing a carbon-carbon triple bond.

The "C$_{3-6}$ cycloalkyl" in the present invention refers to a cyclic alkyl group derived from removing, on a ring on which atoms are all carbon atoms, one hydrogen atom linked to the carbon atoms.

The "C$_{1-6}$ alkoxyl" in the present invention refers to a group derived from "C$_{1-6}$ alkyl" linked to other moieties through —O—, and C$_{1-6}$ alkyl is as defined above.

The "heterocycle" in the present invention refers to a stable 4- to 7-membered monocycle. These heterocycles may be saturated or unsaturated and consist of carbon atoms and 1 to 4 heteroatoms optionally selected from N, O and S, wherein nitrogen and sulfur heteroatoms may be selectively oxidized, and the nitrogen heteroatoms may be selectively quaternized. 5-membered and 6-membered heterocycles, such as furan, imidazole, thiazole, thiadiazole, pyridine, piperidine, pyrazine, and piperazine are preferred.

The compound of the general formula may also exist in other protected forms or in the form of a derivative. These forms are obvious to a person skilled in the art, and should be all included in the scope of the present invention.

Preferably, R1-R6 are optionally selected from hydrogen, methyl, ethyl, propyl, isopropyl, n-butyl, cyano, —COOH, —CONHNHR, —OCH3, —NHCOR, —Br, —Cl, —F,

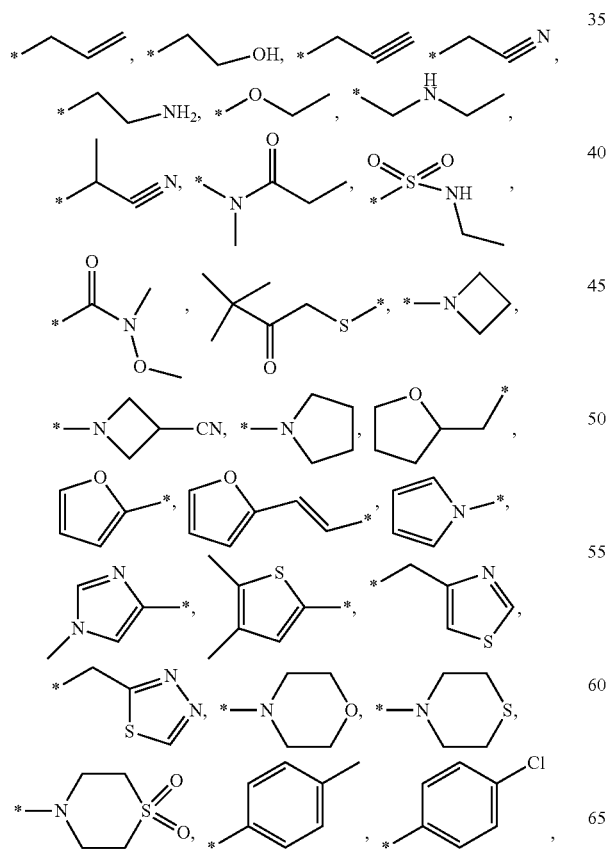

According to the embodiments of the present invention, most preferably, the compound is at least one of the following compounds, or a stereoisomer, pharmaceutically acceptable salt, solvate or prodrug of at least one of the following compounds:

Compound 1

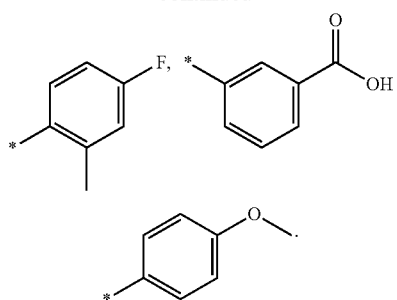

Compound 2

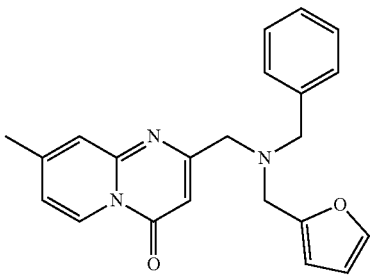

Compound 3

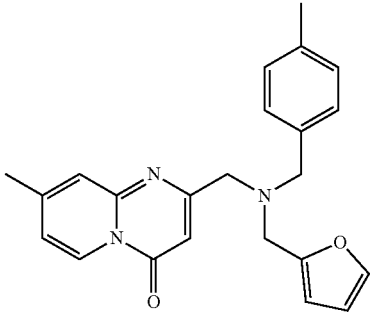

-continued

Compound 4

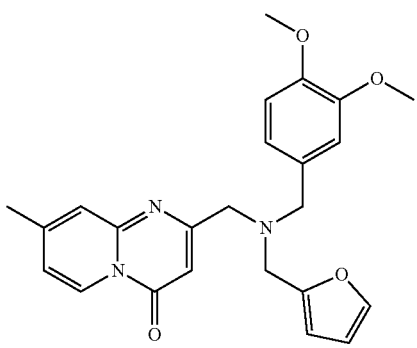

Compound 5

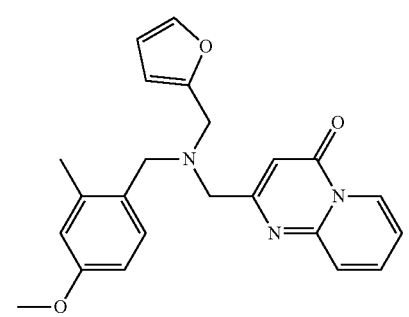

Compound 6

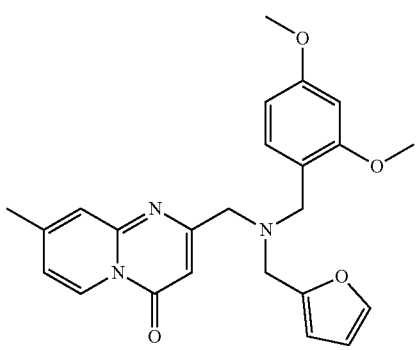

Compound 7

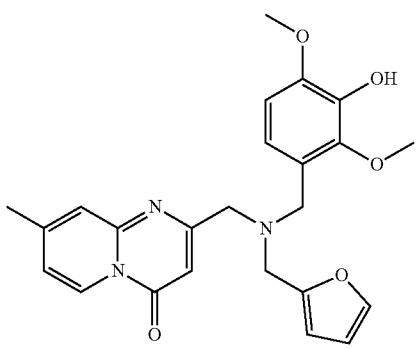

-continued

Compound 8

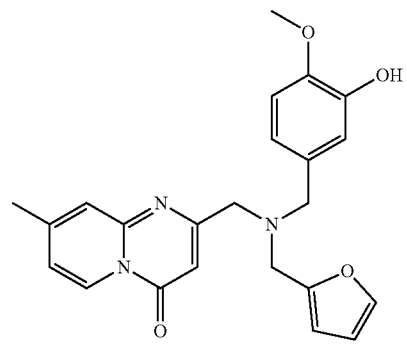

Compound 9

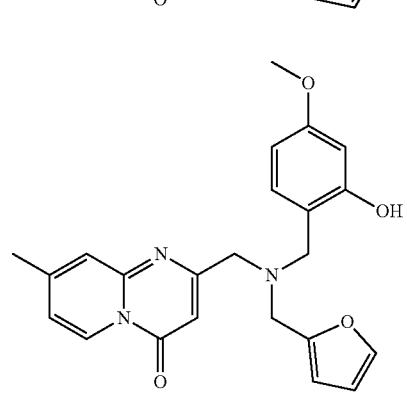

Compound 10

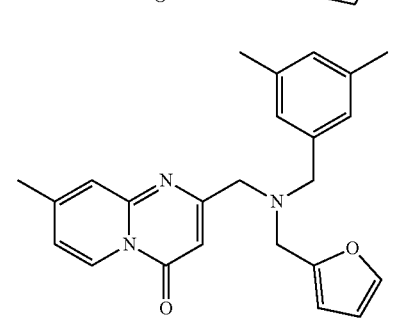

A pharmaceutical composition, including the above-mentioned compound and at least one of pharmaceutically acceptable carriers and excipients.

The pharmaceutical composition uses the compound of the present invention as an active ingredient. The pharmaceutical composition may be prepared according to a method known in the art. The compound of the present invention may be combined with one or more pharmaceutically acceptable solid or liquid excipients and/or adjuvants to prepare any dosage form suitable for human or animal use. The content of the compound of the present invention in the pharmaceutical composition thereof is usually 0.1%-99.9% by weight.

The compound of the present invention or the pharmaceutical composition containing the same may be administered in unit dosage form. The routes of administration may be intestinal or parenteral, such as oral, intravenous injection, intramuscular injection, subcutaneous injection, nasal cavity, oral mucosa, eyes, lungs and respiratory tract, skin, vagina, and rectum; injections are preferred.

The compound of the present invention may be made into ordinary preparations, and may also be made into slow-release preparations, controlled-release preparations, targeted preparations and various microparticle drug delivery systems.

In order to prepare the compound of the present invention into tablets, various excipients known in the art can be widely used, including a diluent, a wetting agent, a binder, a disintegrant, a lubricant, and a glidant. The diluent may be starch, dextrin, sucrose, glucose, lactose, mannitol, sorbitol, xylitol, microcrystalline cellulose, calcium sulfate, calcium hydrogen phosphate, calcium carbonate, etc.; the wetting agent may be water, ethanol, isopropanol, etc.; the binder may be starch slurry, dextrin, syrup, honey, glucose solution, microcrystalline cellulose, acacia mucilage, gelatin mucilage, sodium carboxymethyl cellulose, methyl cellulose, hydroxypropyl methyl cellulose, ethyl cellulose, acrylic resin, Carbomer, polyvinylpyrrolidone, polyethylene glycol, etc.; the disintegrant may be dry starch, microcrystalline cellulose, low-substituted hydroxypropyl cellulose, cross-linked polyvinylpyrrolidone, cross-linked sodium carboxymethyl cellulose, sodium carboxymethyl starch, sodium bicarbonate and citric acid, polyoxyethylene sorbitol fatty acid ester, sodium dodecyl sulfonate, etc.; the lubricant and glidant may be talc, silica, stearate, tartaric acid, liquid paraffin, polyethylene glycol, etc.

The tablets may also be further made into coated tablets, such as sugar-coated tablets, film-coated tablets, enteric-coated tablets, or double-layer tablets and multilayer tablets.

In order to make the administration unit into capsules, the active ingredient, the compound of the present invention, may be mixed with the diluent or glidant, and the mixture may be directly placed in hard or soft capsules. The active ingredient, the compound of the present invention, may also be first made into granules or pellets together with the diluent, binder and disintegrant, and then placed in hard or soft capsules. A variety of diluents, wetting agents, binders, disintegrants, and glidants used to prepare the compound tablets of the present invention may also be used to prepare the compound capsules of the present invention.

In order to prepare the compound of the present invention into injections, water, ethanol, isopropanol, propylene glycol or the mixture thereof may be used as a solvent and an appropriate amount of solubilizer, cosolvent, pH regulator, and osmotic pressure regulator commonly used in the art may be added. The solubilizer or cosolvent may be poloxamer, lecithin, hydroxypropyl-O-cyclodextrin, etc.; the pH regulator may be phosphate, acetate, hydrochloric acid, sodium hydroxide, etc.; the osmotic pressure regulator may be sodium chloride, mannitol, glucose, phosphate, acetate, etc. To prepare freeze-dried powder injections, mannitol, glucose, etc. may also be added as proppants.

In addition, if necessary, colorants, preservatives, flavors, correctives or other additives may also be added to the pharmaceutical preparations.

Use of the compound or the pharmaceutical composition in preparation of drugs for preventing and treating of proliferative diseases, wherein the proliferative diseases are cancers, and the cancers are breast cancers or ovarian cancers.

The present invention relates to the use of the compound and the pharmaceutical composition containing the same to prevent or treat cell proliferative and cell regenerative diseases. Specifically, the present invention relates to an application of using the compound and the pharmaceutical composition containing the same to prevent and treat cancers.

In addition, the use of the compound and the pharmaceutical composition containing the same to prevent or treat diseases by inhibiting HIF-2α protein is involved. Specifically, the present invention relates to the application of using the compound and the pharmaceutical composition containing the same to prevent and treat cancers.

The "diseases" in the present invention include, but are not limited to, the following diseases:

cancers, including breast cancer, ovarian cancer, bladder cancer, brain cancer, colon cancer, rectal cancer, kidney cancer, liver cancer, lung cancer, pancreatic cancer, adrenal cancer, prostate cancer, gastric cancer, vagina cancer, cervical cancer, endometrial cancer, thyroid cancer and skin cancer, etc.;

lymphohematopoietic system tumors, including acute lymphoblastic leukemia, B-cell lymphoma and Burketts lymphoma, etc.;

myeloid hematopoietic system tumors, including acute and chronic myelogenous leukemia and promyelocytic leukemia;

tumors of mesenchymal origin, including fibrosarcoma and rhabdomyosarcoma; and other tumors, including melanoma, seminoma, teratoma, neuroblastoma, glioma, etc.

In order to achieve the purpose of medication and enhance the therapeutic effect, the drugs or pharmaceutical composition of the present invention can be administered using any known administration method.

The administration dosage of the pharmaceutical composition of the compound of the present invention can vary widely, depending on the nature and severity of the disease to be prevented or treated, the individual conditions of the patient or animal, the route of administration, the dosage form and the like. Generally speaking, the appropriate daily dosage range of the compound of the present invention is 0.001-150 mg/Kg body weight, preferably 0.1-100 mg/Kg of body weight, more preferably 1-60 mg/Kg of body weight, and most preferably 2-30 mg/Kg of body weight. The above-mentioned dosage can be administered in one dosage unit or divided into several dosage units, depending on the doctor's clinical experience and the administration regimen including the use of other treatment means.

The compound or composition of the present invention can be taken alone or combined with other therapeutic drugs or symptomatic drugs. When the compound of the present invention has a synergistic effect with other therapeutic drugs, its dosage should be adjusted according to the actual situation.

The term "prodrug" as used in the present invention represents a compound which can be converted to a compound represented by formula (I) in vivo. Such conversion is affected by the hydrolysis of the prodrug in the blood or the enzymatic conversion of the prodrug into the parent structure in the blood or tissue.

"Pharmaceutically acceptable salt" used in the present invention refers to the organic and inorganic salts of the compound of the present invention. Pharmaceutically acceptable salts formed with non-toxic acids include, but are not limited to, inorganic acid salts formed by reaction with amino groups, such as hydrochloride, hydrobromide, phosphate, sulfate and perchlorate salts; and organic acid salts, such as acetate, oxalate, maleate, tartrate, citrate, succinate and malonate salts; or these salts obtained by other methods such as ion exchange recorded in books and literatures. Other pharmaceutically acceptable salts include adipate, alginate, ascorbate, aspartate, benzenesulfonate, benzoate, bisulfate, borate, butyrate, camphorate, camphor sulfonate, cyclopentyl propionate, digluconate, lauryl sulfate, ethanesulfonate, formate, fumarate, glucoheptonate, glycerophosphate, gluconate, hemisulfate, heptanoate, caproate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectate, persulfate, 3-phenylpropionate, picrate, pivalate, propionate, stearate, thiocyanate, p-toluenesulfonate, undecanoate, valerate salts, etc. Salts obtained with appropriate bases include salts of alkali metals, alkaline earth metals, ammonium and N+(C1-4 alkyl)4. The present invention also contemplates the quaternary ammonium salts formed with any compound containing the N group. Water-soluble or oil-soluble or dispersed products can be obtained by quaternization. Salts of alkali metals or alkaline earth metals include sodium, lithium, potassium, calcium, magnesium salts, and the like. Pharmaceutically acceptable salts further include appropriate, non-toxic ammonium, quaternary ammonium salts and amine cations formed with counterions, such as halides, hydroxides, carboxylates, sulfates, phosphates, nitrates, C1-8 sulfonates and aromatic sulfonates.

The "solvate" of the present invention refers to an association substance formed by one or more solvent molecules and the compound of the present invention. Solvents that form solvates include, but are not limited to, water, isopropanol, ethanol, methanol, dimethyl sulfoxide, ethyl acetate, acetic acid, and aminoethanol. The term "hydrate" refers to an association substance formed with a solvent molecule being water.

When the solvent is water, the term "hydrate" may be applicable. According to an embodiment of the present invention, one compound molecule of the present invention may be combined with one water molecule, to form such as a monohydrate; according to an embodiment of the present invention, one compound molecule of the present invention may be combined with more than one water molecules, to form such as a dihydrate; and according to an embodiment of the present invention, one compound molecule of the present invention can be combined with less than one water molecule, to form such as a hemihydrate. It should be noted that the hydrate of the present invention retains the bioavailability of the compound in a non-hydrated form.

As used in the present invention, the term "prevention" refers to the reduction of the risk of suffering from a disease or disorder (i.e.: stopping the development of at least one clinical symptom of the disease in a subject, who may face or predispose to face the disease, but has not experienced or exhibited symptoms of the disease).

The term "treatment" of any disease or condition, in some embodiments, refers to amelioration of the disease or condition (i.e. slowing down or preventing or alleviating the development of the disease or at least one of its clinical symptoms). In other embodiments, "treatment" refers to alleviation or amelioration of at least one physical parameter, including physical parameters that may not be perceived by the patient. In other embodiments, "treatment" refers to the regulation of the disease or condition physically (for example, stabilizing perceptible symptoms) or physiologically (for example, stabilizing the parameters of the body) or both. In other embodiments, "treatment" refers to prevention or delay of the onset, occurrence or deterioration of a disease or condition.

Compared with the prior art, the invention has the following characteristics and advantages over the existing technologies:

1. The applicant proposed for the first time through research that the small molecule inhibitor of the present invention mainly inhibits the proliferation of tumor cells by inhibiting HIF-2α protein, and can further inhibit the growth of CSCs with high expression of HIF-2α, and can be used as a new anti-tumor drug to completely eliminate tumors and stem cells.

2. The HIF-2α small molecule inhibitor of the present invention uses pyrimido [1,2-a] pyridine as the parent nucleus, belongs to the aromatic amines, and has reduced toxicity as compared with aliphatic amines.

3. The small molecule inhibitor of the present invention has no obvious inhibitory effect on the expression of HIF-1α, and it is confirmed that the small molecule inhibitor is an inhibitor specific for HIF-2α and has targeted specificity.

4. The existing HIF-2α inhibitors are mainly used for kidney cancer, while the compound of the present invention has a broad anti-cancer spectrum and has a growth inhibitory effect on a variety of cancer cells, such as ovarian cancer and breast cancer.

5. The compound of the present invention can be used in combination with chemotherapeutic drugs such as paclitaxel and cisplatin to improve its anti-tumor effect.

In summary, the compounds disclosed in the present invention have good application prospects in the prevention or treatment of proliferative diseases, especially cancer, in terms of the structure and mechanism of action.

DETAILED DESCRIPTION OF EMBODIMENTS

Hereinafter, the above-mentioned content of the present invention will be further described in detail through specific implementations in the form of examples. However, it should not be understood that the scope of the above-mentioned subject matter of the present invention is limited to the following examples. All technologies implemented based on the foregoing content of the present invention belong to the scope of the present invention.

Example 1: The Structure and Identification of the HIF-2α Inhibitor

Figure 1:
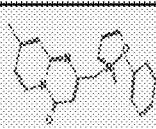
FIG. 1 shows the result of docking using the molecular simulation drug design software MOE.

The applicant used the molecular simulation drug design software MOE to screen the pharmacophores and perform molecular docking, and conducted experimental verification based on the final superior structure from docking, thereby screening out the HIF-2α inhibitor of the present invention, which shows that compounds with pyrimido [1,2-a] pyridine as the parent nucleus have the effect of HIF-2α inhibitor, but changes in the substituents on the parent nucleus can lead to different action targets and also possible different purposes of final clinical indications to be treated. Such compounds have a higher avidity for the PAS region (as shown in FIG. 1, S=−10.1898). The applicant entrusted Topscience Co., Ltd. to synthesize HIF-2α inhibitors. The structures of the HIF-2α inhibitors are as follows:

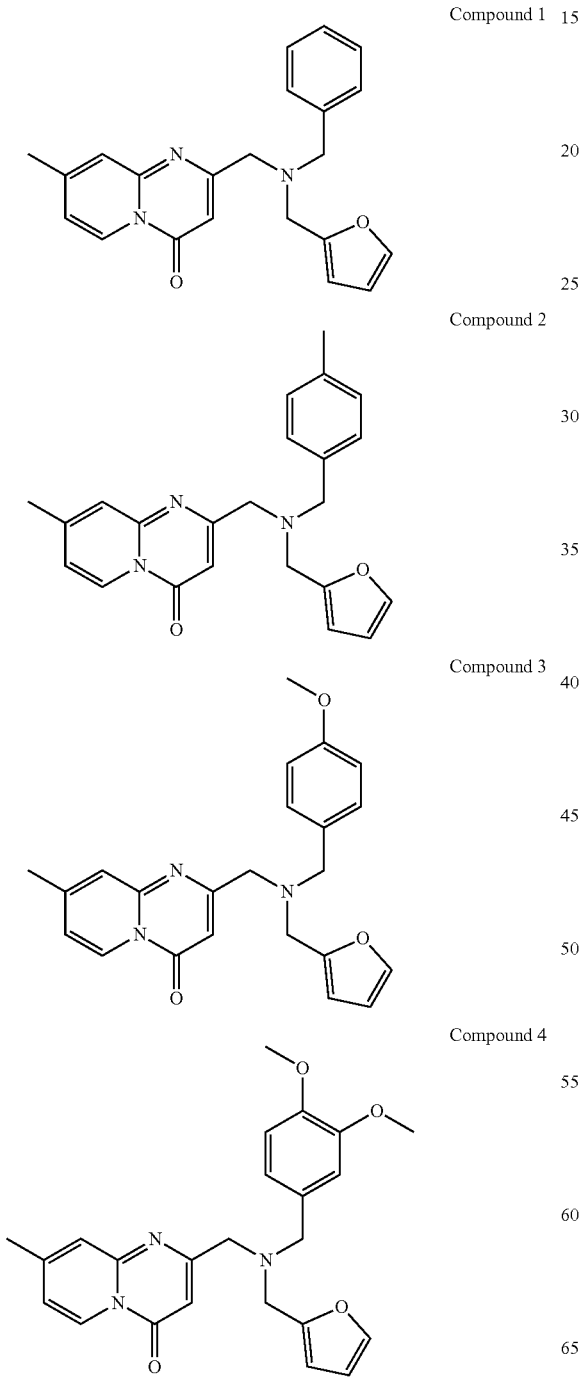

Compound 1

Compound 2

Compound 3

Compound 4

-continued

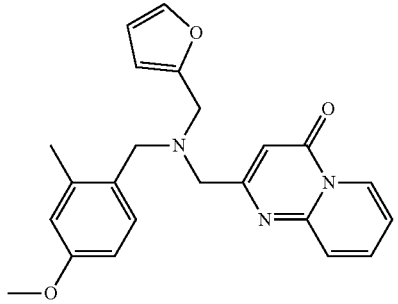

Compound 5

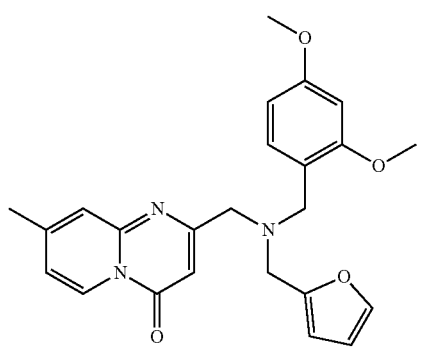

Compound 6

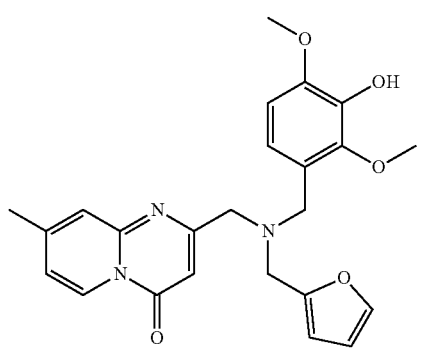

Compound 7

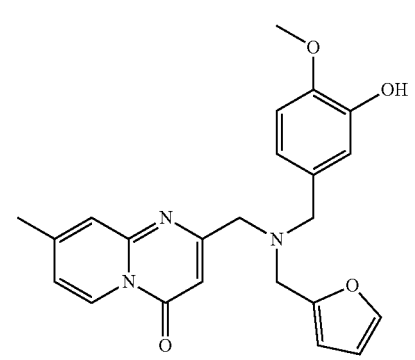

Compound 8

-continued

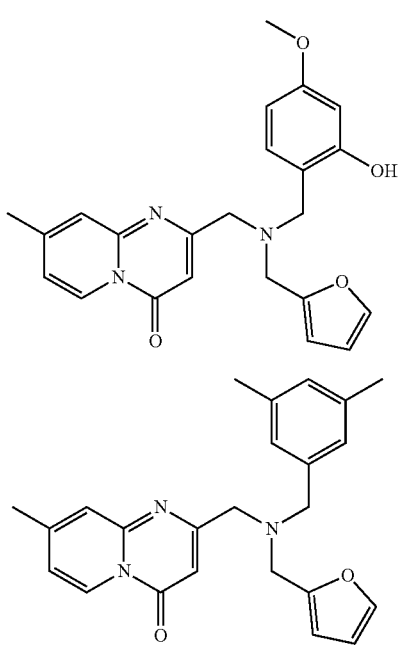

Compound 9

Compound 10

Figure 2:
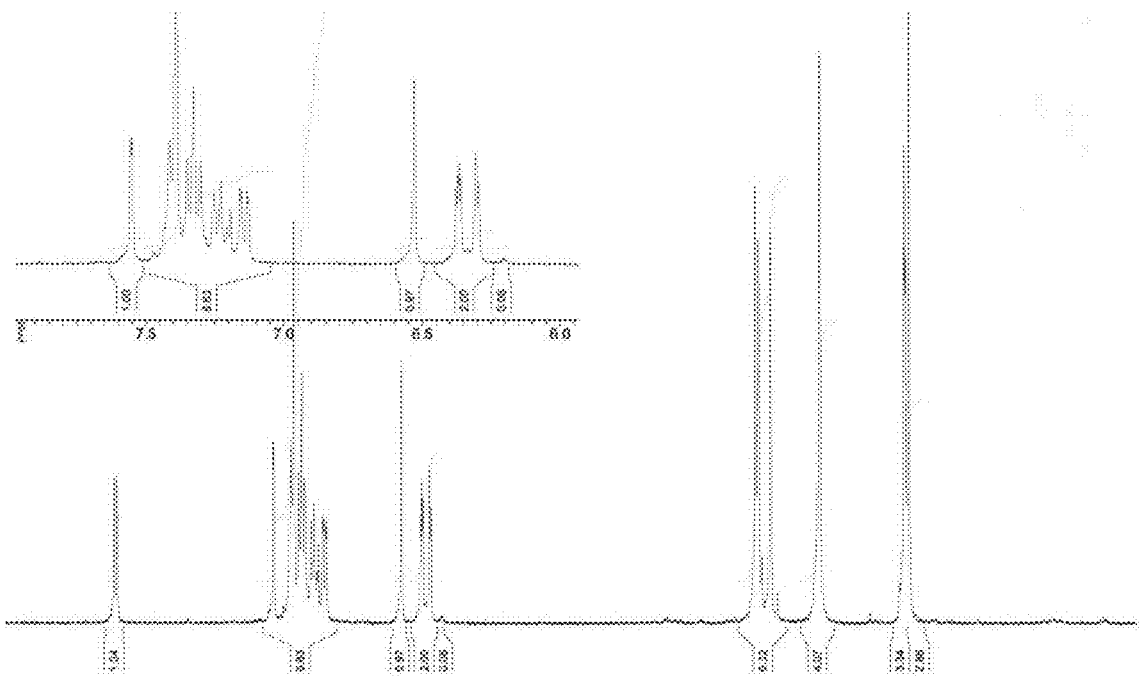
FIG. 2 shows the hydrogen spectrum of the HIF-2α inhibitor compound 1 of the present invention.
Figure 3:
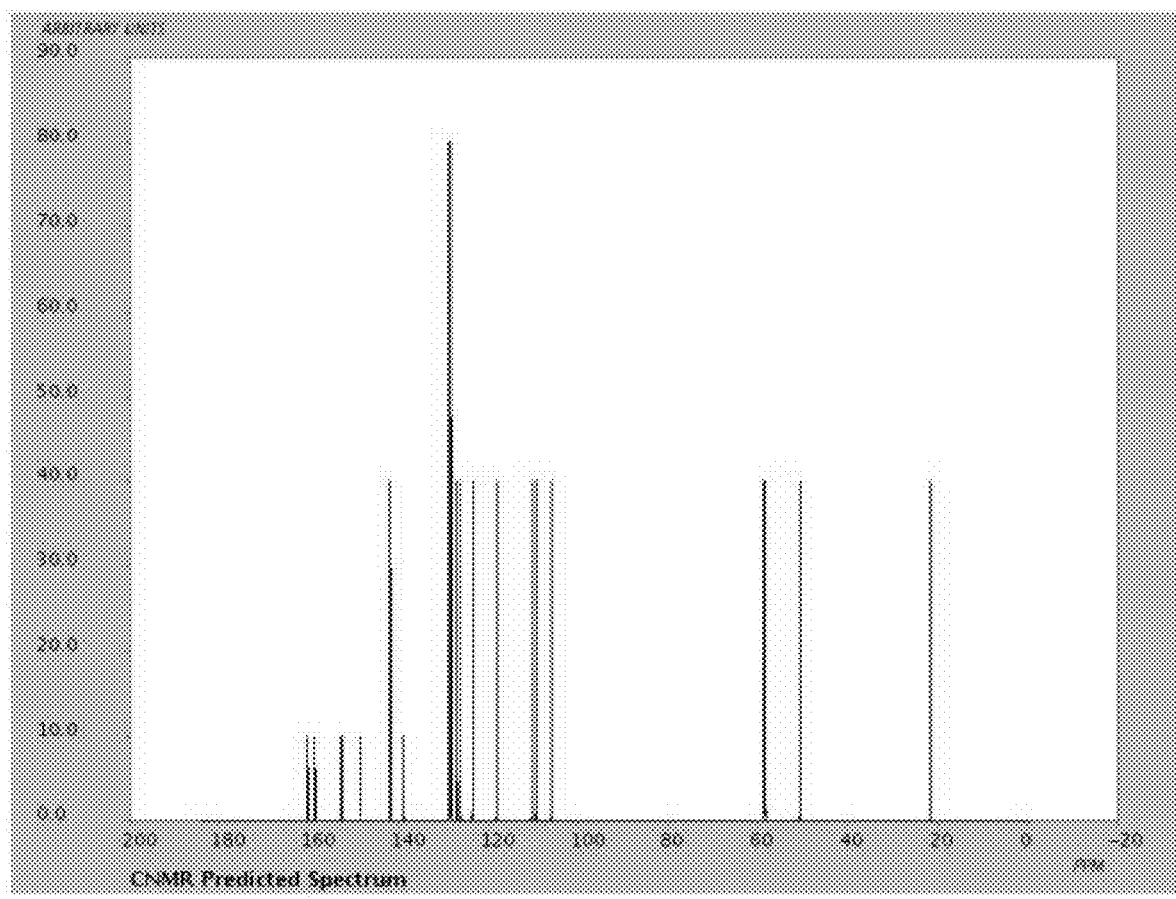
FIG. 3 shows the carbon spectrum of the HIF-2α inhibitor compound 1 of the present invention.

The hydrogen spectrum and carbon spectrum of Compound 1 (ComA) are detected, as shown in FIG. 2 and FIG. 3, respectively.

Example 2: Anti-Tumor Activity of the HIF-2α Inhibitor

1 Experimental Materials
1.1 Cells and Reagents

Human breast cancer cell MCF-7, and human ovarian cancer cell OVCAR-3. DMEM, DMEM/F12 medium, 1640 medium, Trypsin-EDTA (0.05%); B27, protein maker, EGF, bFGF, fetal bovine serum (FBS), dimethyl sulfoxide (DMSO), paclitaxel (PTX), cisplatin (DDP), methyl thiazolyl tetrazolium (MTT), Cell proliferation and toxicity detection kit (Cell counting kit-8, CCK-8), rabbit anti-human HIF-1α monoclonal antibody; rabbit anti-human HIF-2α monoclonal antibody; RIPA cell lysis solution, Protease inhibitor cocktail, and goat anti-rabbit IgG secondary antibody.

2 Experimental Method
2.1 Cell Culture

MCF-7 and OVCAR-3 cells were taken out from liquid nitrogen, thawed in a water bath at 37° C., and centrifuged at 1000 rpm for 5 min, the supernatant was removed, 1 ml of DMEM medium with 10% fetal bovine serum was added to MCF-7 cells, the cell suspension was transferred into a 25 cm2 cells culture flask, and a medium with 10% fetal bovine serum was added for culture.

2.2 Balloon Cell Induction

When MCF-7 or OVCAR-3 cells grew to 70%-80%, the medium was discarded, PBS was added for washing 3 times, and trypsin was added for digestion for 1 min; the DMEM medium containing 10% fetal calf serum was added to stop the digestion, centrifuged at 1000 rpm for 5 min, the supernatant was discarded, PBS was added to resuspend cells, centrifuged at 1000 rpm for 5 min, the supernatant was discarded, 2 ml DMEM-F12 conditioned medium was added to resuspend cells, and the cells were cultured in suspension at 37° C., 5% CO2 in a constant-humidity environment.

2.3 MTT, CCK8 Cell Proliferation Analysis

Well-growing human breast cancer MCF-7 cells, human breast cancer stem cell-like cell MCF-7 MS cells, human ovarian cancer OVCAR-3 cells, human ovarian cancer stem cell-like cell OVCAR-3 cells were taken, digested, resuspended, and inoculated in a 96-well plate with the number of cells per well being $5\times10^3$; after 24 hours of culture, different concentrations of ComA, ComA combined with PTX, or ComA combined with DDP were administrated for treating the cells for 48 hours, with 3 replicate wells for each concentration; 5 mg/ml of MTT/cck8 was added for treatment for 2 h, followed by shaking for 10 min in a shaker; the absorbance at 570 nm (for measuring MTT)/450 nm (for measuring CCK8) was measured with a microplate reader, the inhibition rate was calculated according to the formula: inhibition rate %=[1−(dosing well-zero adjustment well)/(control well-zero adjustment well)]*100%; IC50 was calculated with SPSS16.0 software, and the experiment was repeated three times.

Figure 4:
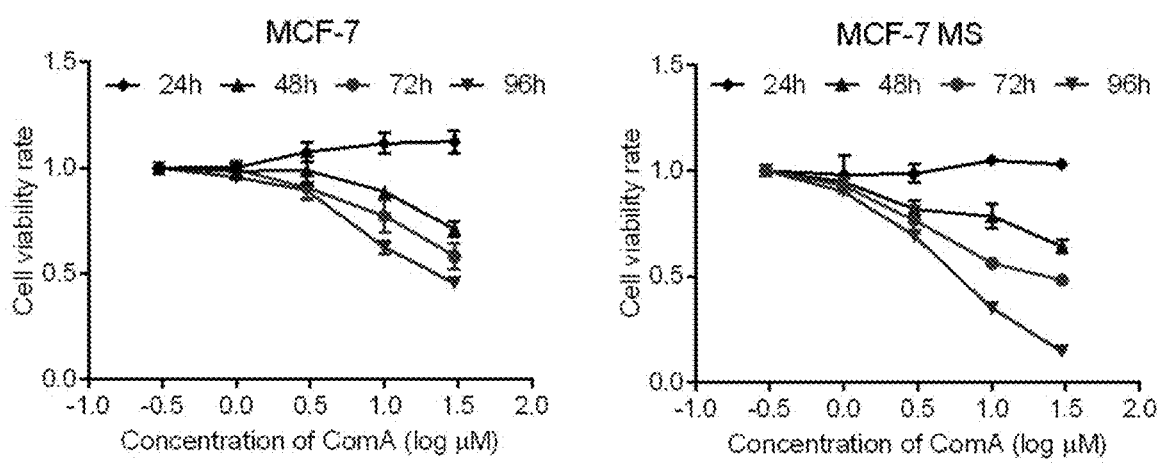
FIG. 4 shows the changes of proliferation inhibited by the HIF-2α inhibitor of the present invention on breast cancer MCF-7 cells and their induced stem cell MCF-7 MS cells.
Figure 5:
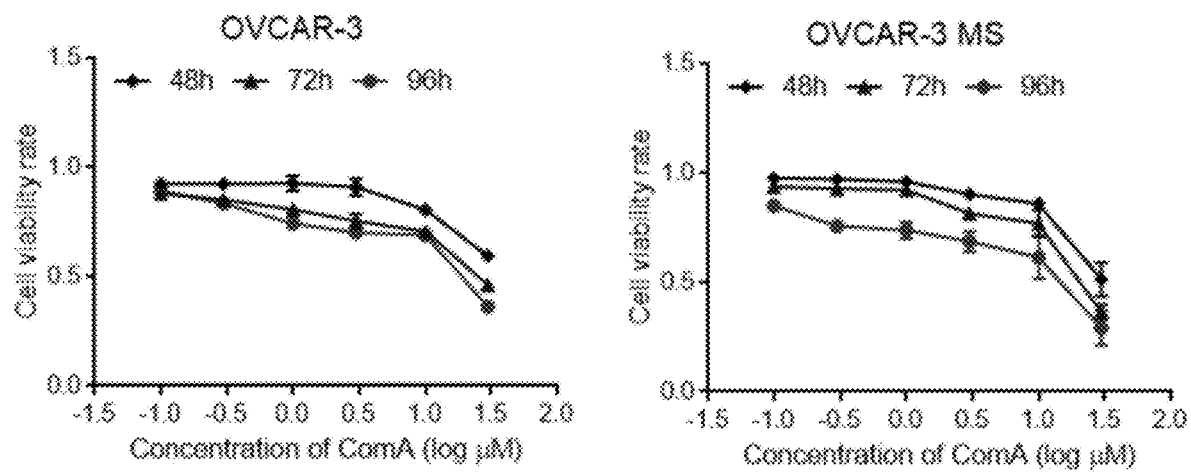
FIG. 5 shows the changes of proliferation inhibited by the HIF-2α inhibitor of the present invention on ovarian cancer OVCAR-3 cells and their induced stem cells OVCAR-3 MS cells.

Experimental Results and Conclusions:

The compound ComA has anti-tumor activity. The proliferation results obtained by MTT/cck8 are shown in FIG. 4. The compound has obvious inhibitory activity on human breast cancer MCF-7 cells and human breast cancer stem cell-like MCF-7 MS cells; and has obvious inhibitory activity on human ovarian cancer OVCAR-3 cells and ovarian cancer stem cell-like OVCAR-3 MS cells (as shown in FIG. 5), and the compound ComA's anti-tumor cell and anti-tumor stem cell activity is obviously time-dependent.

Figure 6:
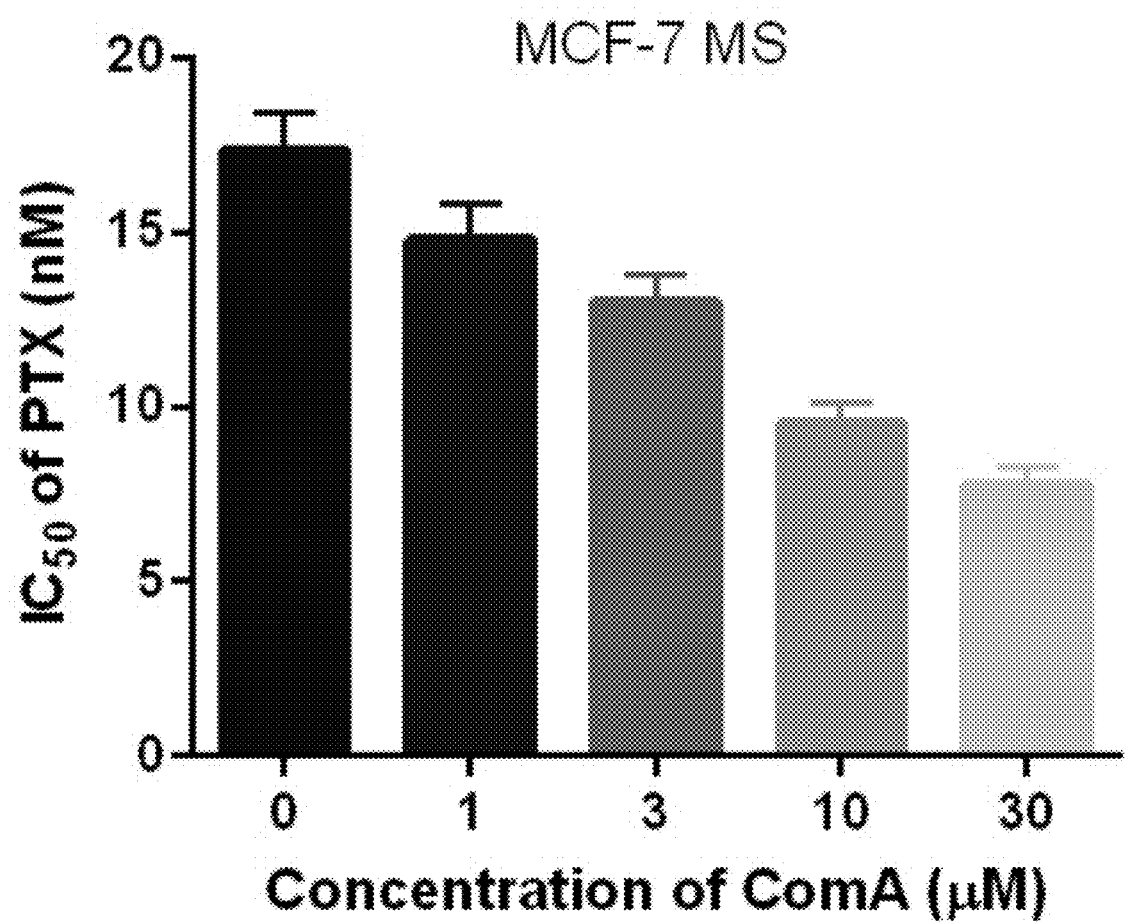
FIG. 6 shows that the HIF-2α inhibitor of the present invention synergistically sensitizes the inhibitory effect of paclitaxel on breast cancer stem cells MCF-7 MS cells.
Figure 7:
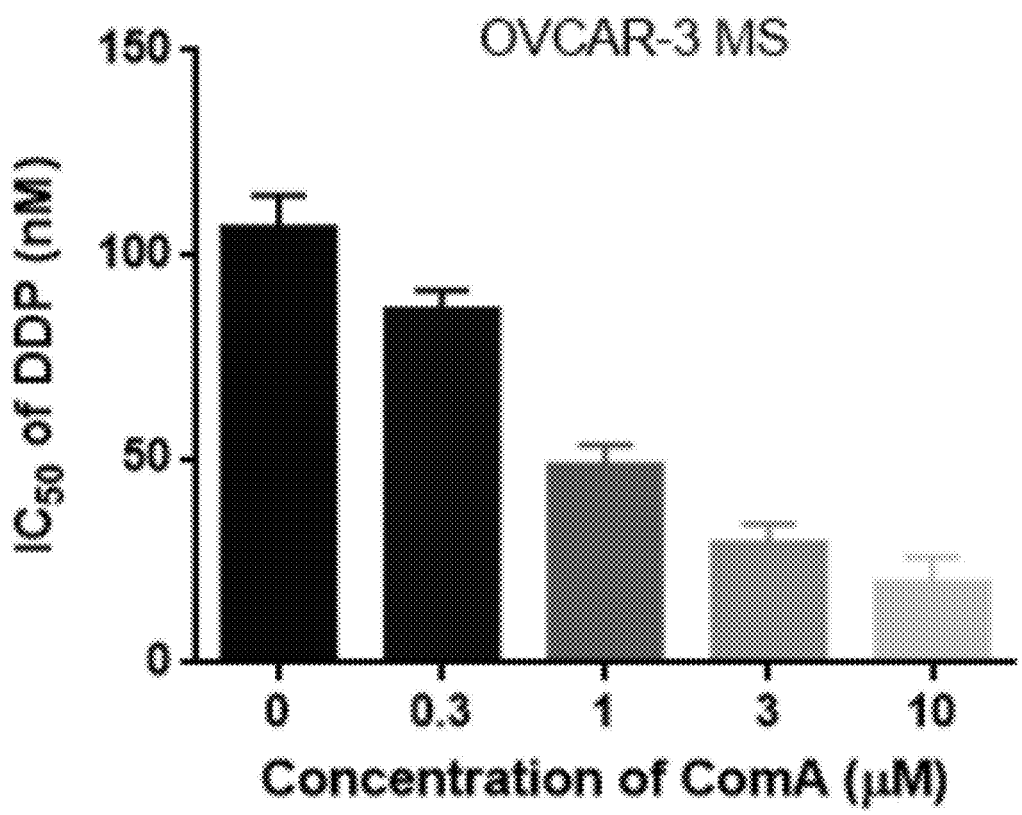
FIG. 7 shows that the HIF-2α inhibitor of the present invention synergistically sensitizes the inhibitory effect of paclitaxel on ovarian cancer stem cells OVCAR-3 MS cells.

The compound ComA can enhance the inhibitory effect of the chemotherapeutic drug paclitaxel (PTX) on human breast cancer stem cell-like MCF-7 MS cells, and as the dose of ComA increases, the synergistic effect reduces the IC50 value of PTX (as shown in FIG. 6). ComA can enhance the inhibitory effect of the chemotherapeutic drug cisplatin (DDP) on human ovarian cancer stem cell-like OVCAR-3 MS cells, and as the dose of ComA increases, the synergistic effect reduces the IC50 value of DDP (as shown in FIG. 7).

2.4 Western Blot Analysis
2.4.1 Extraction of Total Cell Protein

The human breast cancer stem cell-like MCF7 MS cells were divided into control (Ctrl) group, PTX alone treatment group, ComA alone treatment group, and ComA combined with PTX treatment group, treated for 48 h, and then collected; the cells were washed twice with pre-cooled 1×PBS, and PBS was discarded; 100-200 μl RIPA cell lysis solution (RIPA cell lysis solution:Protease inhibitor cocktail=250:1) was added according to the amount of cells; the mixture was transferred to an EP tube for lysis on ice for 40-60 min, and centrifuged at 4° C. at 12000 rpm/min for 15 minutes; and the supernatant was taken and stored at −80° C. for later use.

2.4.2 BCA Method for Protein Quantification

Protein standard curve was prepared (in a 96-well plate), with the configuration system and absorbance shown in the table below, wherein the protein solution was placed at 37° C. and shaken for 30 min, the OD value was measured at 570 nm wavelength, and the protein standard curve was drawn: the abscissa being the standard protein content, and the ordinate being the absorbance value (OD value) under the 570 nm wavelength, thereby drawing a standard curve.

2.4.3 Sorting Out Protein Samples

The samples were treated with 6× protein loading buffer. According to the quantified protein concentration, 30 μl:50 μg protein sample per well was loaded, the well was filled with PBS up to 30 μl when the sample was insufficient, and the samples were denatured in a metal bath at 100° C. for 10 min.

2.4.4 Electrophoresis, Trans-Blotting

A glass plate was washed clean, dried, and placed on a gel making rack; 8%, 10% and 12% separating gels and 5% concentrating gel were formulated, the separating gel and concentrating gel were infused in sequence respectively, a clean comb was inserted in the concentrating gel immediately, and the gels were polymerized at room temperature for 15 min. After the concentrating gel was solidified, the gel rack was put in an electrophoresis tank, 500 mL of 1× electrophoresis buffer was added, the gel rack was soaked for 20 min, and the samples were loaded. The electrophoresis was run at a constant voltage of 60 V, until the bromophenol blue indicator moved to the boundary between the concentrating gel and the separating gel, the voltage was adjusted to 100 V, and when the bromophenol blue indicator moves to 1 cm from the bottom of the gel, the electrophoresis was stopped; and the gel was taken out and put in a trans-blotting buffer for recovery. The gel was cut, and the 0.45 μm/0.22 μm PVDF membrane was scissored to the same size, soaked in methanol for 30 s, and soaked in the trans-blotting buffer for 5 min. The PVDF membrane was covered on the corresponding target position on the gel. 6 pieces of filter paper with the same size as a trans-blotting clamp were scissored, and immersion wet with the transfer buffer, and a glass rod was used to drive out the bubbles. The sandwich in the order of sponge, filter paper, gel, PVDF membrane, filter paper, and sponge was assembled. The assembled trans-blotting sandwich was placed in a trans-blotting tank in the direction that the gel was at the negative electrode and the PVDF membrane was at the positive electrode. The trans-blotting voltage and trans-blotting time were determined according to the molecular weight of the target protein. The trans-blotting voltage was at 60-70 V and trans-blotting was performed at 4° C. for 2 h-3 h.

2.4.5 Blocking, Antibody Hybridization, and Development

5% BSA was used for blocking at room temperature in a shaker for 1 h, and the membrane was washed with 1×TBST for 5 min×3 times. The primary antibodies were diluted with antibody diluents in different ratios (for the rabbit anti-human HIF-1α monoclonal antibody, the dilution ratio being 1:2000; and for the rabbit anti-human HIF-2α monoclonal antibody, the dilution ratio being 1:2000), and incubated in a shaker at 4° C. overnight. The membrane was washed with 1×TBST for 5 min×3 times; HRP-labeled goat anti-rabbit IgG secondary antibody was diluted with 1×TBST at 1:20000, incubated under shaking at room temperature for 1 h, then the membrane was washed with TBS for 5 min×3 times; ECL imaging System was used for luminescence development, and FluorChem V2.0 software (Alpha Innotech Corp, USA) was used for analysis of band gray values for statistical analysis.

Figure 8:
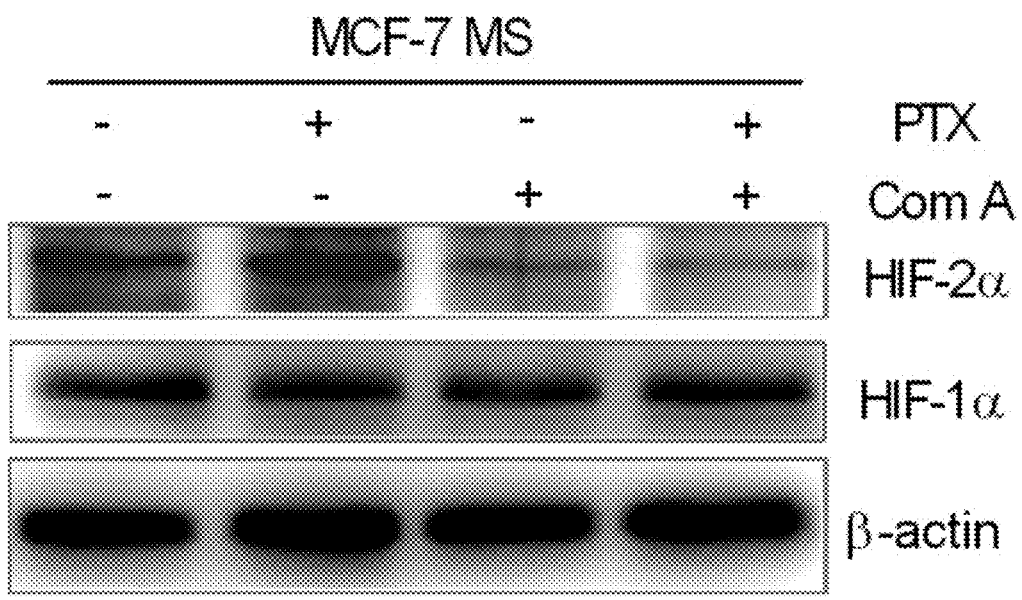
FIG. 8 shows Western blot patterns showing the changes of HIF-2α and HIF-1α after the HIF-2α inhibitor of the present invention is used alone and in combination with paclitaxel in breast cancer stem cells MCF-7 MS cells.

Experimental Results and Conclusions:

After MCF-7 MS cells were treated with compound ComA alone, and compound ComA combined with PTX, the results of expression of HIF-2α were shown in FIG. 8. ComA alone and ComA combined with PTX obviously inhibited the expression of HIF-2α, and ComA had no obvious inhibitory effect on the expression of HIF-1α. It is confirmed that ComA is an inhibitor specific for HIF-2α.

Only the preferred Examples of the present invention are described above, and are not intended to limit the present invention, and various modifications and changes can be made to the present invention for those skilled in the art. Any modification, equivalent substitution, improvement and the like made within the spirit and principle of the present invention are intended to be included within the scope of the present invention.

The invention claimed is:

1. A method of treating tumors by inhibiting HIF protein, said method comprising administering to a patient a pharmaceutical composition comprising a compound represented by formula (I),

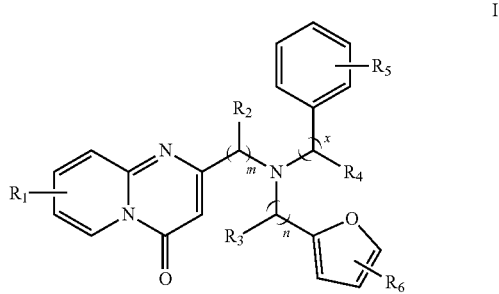

wherein:
m represents 0, 1, 2 or 3; n represents 0, 1, 2 or 3; and x represents 0, 1, 2 or 3;
R1 is an optionally mono- or poly-substituted substituent at any position on a parent nucleus based on pyrimido [1,2-a]pyridine; R2, R3 and R4 are substituents on any carbon atoms on a 2-position branch of a pyrimido[1, 2-a]pyridine-based parent nucleus ring; R5 is an optionally mono- or poly-substituted substituent at any position on a benzene ring; R6 is an optionally mono- or poly-substituted substituent at any position on a furan ring; the substituted substituent is one or more selected from C1-6 alkyl, halogen-, hydroxyl-, carboxyl- or cyano-substituted C1-6 alkyl, halogen-, hydroxyl-, carboxyl- or cyano-substituted C3-6 cycloalkyl, C1-6 alkoxyl, halogen-, hydroxyl-, carboxyl- or cyano-substituted C1-6 alkoxyl, C2-6 alkenyl, halogen-, hydroxyl-, carboxyl- or cyano-substituted C2-6 alkenyl, nitro, amino, C1-6 alkyl-substituted amino, halogen, cyano, sulfo, hydroxyl, carboxyl, phenyl, and heterocyclyl; and two adjacent substituent groups and linking atoms form a three-membered, four-membered, five-membered or multi-membered ring structure,
wherein said pharmaceutical composition inhibits HIF expression, renders the tumor sensitive to hypoxic environments and inhibits tumor cell growth.

2. The method of treating tumors according to claim 1, wherein R1-R6 are selected from hydrogen, methyl, ethyl, propyl, isopropyl, n-butyl, cyano, —COOH, —CONHNHR, —OCH3, —NHCOR, —Br, —Cl, —F,

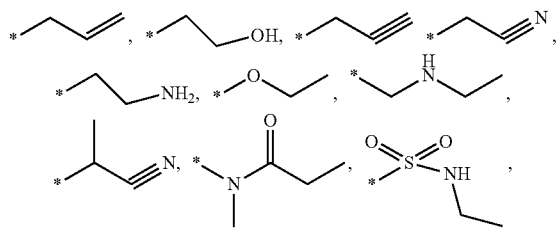

17
-continued
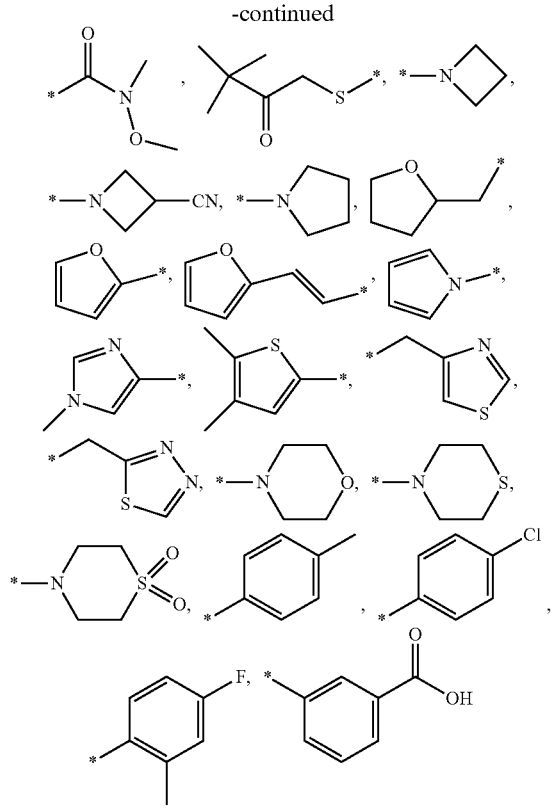
18
-continued
3. The method of treating tumors according to claim 1, wherein the compound is
4. The method of treating tumors according to claim 1, wherein the tumors are the result of breast cancers or ovarian cancers.
* * * * *